United States Patent [19]

Kruger et al.

[11] Patent Number: 4,612,034

[45] Date of Patent: Sep. 16, 1986

[54] HERBICIDAL FORMULATION

[75] Inventors: Paul J. Kruger, Middlesex; George Schwartzkopf, Franklin Township, Bexar County, both of N.J.

[73] Assignee: J. T. Baker Chemical Company, Phillipsburg, N.J.

[21] Appl. No.: 554,769

[22] Filed: Nov. 28, 1983

Related U.S. Application Data

[63] Continuation-in-part of Ser. No. 453,810, Dec. 27, 1982, abandoned.

[51] Int. Cl.⁴ ............................................. A01N 59/24
[52] U.S. Cl. .......................................... 71/80; 71/65; 71/86
[58] Field of Search ............................. 71/80, 86, 65

[56] References Cited

U.S. PATENT DOCUMENTS

| | | | |
|---|---|---|---|
| 1,997,750 | 4/1935 | Sauchelli | 71/65 X |
| 2,269,397 | 1/1942 | Osborne | 71/65 X |
| 3,414,398 | 12/1968 | Chacon | 71/65 |
| 3,799,758 | 3/1974 | Franz | 71/86 |

OTHER PUBLICATIONS

Al-Jaff et al., Ann. Appl. Biol. vol. 101 (1982), pp. 323–329.
Federal Register Notice, vol. 46, No. 139 (Jul. 21, 1981), p. 37509.

*Primary Examiner*—Catherine L. Mills
*Attorney, Agent, or Firm*—George W. Rauchfuss, Jr.; Salvatore R. Conte

[57] ABSTRACT

An improved herbicidal formulation comprising a mixture of the isopropylamine salt of glyphosate and an effective potentiating amount of an ammonium, quaternary alkyl ammonium, alkali metal or alkaline earth metal thiocyanate.

2 Claims, No Drawings

HERBICIDAL FORMULATION

CROSS-REFERENCE TO RELATED APPLICATION

This is a continuation-in-part of our copending application Ser. No. 453,810, filed Dec. 27, 1982, now abandoned.

FIELD OF THE INVENTION

The invention relates to enhancing the herbicidal activity of the isopropylamine salt of glyphosate by certain thiocyanates.

BACKGROUND OF THE INVENTION

The isopropylamine salt of glyphosate is a known herbicide which is currently registered for such purpose with the Environmental Protection Agency (EPA). Thiocyanates, in general, have found several agricultural applications such as herbicides, crop desiccants and defoliants, adjuvants and the like.

In some cases, active agricultural chemicals have been shown to be more effective in combination than when applied individually. The result is often termed "potentiation" or "synergism" since the combination demonstrates a potency or activity level exceeding that which it would be expected to have, based on a knowledge of the individual potencies of the components.

The present invention resides in the discovery that the herbicidal activity of the isopropylamine salt of glyphosate is markedly enhanced when used in combination with certain thiocyanates, particularly ammonium thiocyanate.

DETAILED DESCRIPTION OF THE INVENTION

It has now been found that synergism in herbicidal activity is exhibited by the isopropylamine salt of glyphosate and a thiocyanate compound selected from the group consisting of ammonium, quaternary alkyl ammonium, alkali metal and alkaline earth metal thiocyanate. In addition to ammonium thiocyanate, other thiocyanates that may be employed are, for example, alkali metal thiocyanates, such as sodium and potassium thiocyanate, alkaline earth metal thiocyanates such as magnesium and calcium thiocyanate, and quaternary alkyl ammonium thiocyanates such as trialkyl and tetraalkyl ammonium thiocyanates, e.g., trimethyl dodecyl ammonium thiocyanate and the like. The preferred thiocyanates are ammonium, sodium and potassium thiocyanate, ammonium thiocyanate being most preferred.

A particularly suitable aqueous formulation of ammonium thiocyanate for use herein is the commercial product registered with the Environmental Protection Agency (EPA) as a spray adjuvant and available under the trade name "Intensify" from the J. T. Baker Chemical Co. This product is a flowable formulation consisting of an aluminum hydroxide gel suspension of ammonium thiocyanate containing about 44.5% ammonium thiocyanate.

Glyphosate is the common name for the acid, N-(phosphonomethyl)glycine. The isopropylamine salt of glyphosate is registered with the EPA for approval as a herbicide. This salt is the active ingredient (A.I.) in the liquid formulation commercially available under the trade name "Roundup" from the Monsanto Agricultural Products Company, St. Louis, Mo. It is a herbicide recommended for postemergence control of a broad spectrum of annual and perennial grass and broadleaf weeds. Typical weeds include (i) annual grasses such as, for example, annual bluegrass, crabgrass species, field sandbur, foxtail species, shattercane and the like; (ii) annual broadleaves such as, for example, common lambsquarter, common ragweed, prickly lettuce, smooth pigweed, velvetleaf and the like; (iii) perennial grasses such as, for example, bermudagrass, Kentucky bluegrass, johnsongrass, paragrass and the like; and (iv) perennial broadleaves such as, for example, Canada thistle, common mullein, milkweed, silverleaf nightshade and the like.

The aforementioned commercial formulation "Roundup" is a water soluble liquid concentrate of the isopropylamine salt of glyphosate (A.I.) containing 4 pounds A.I. per U.S. gallon (equivalent to 3 lbs of the corresponding acid/gal.). The concentrate is generally diluted with water at the manufacturer's recommended concentration for the specific weed control program and generally applied in 20 to 60 gallons of water per treated acre with ground equipment using standard herbicide sprayers. For example, 2–3 quarts of Roundup (2–3 lbs. A.I.) in 20–60 gallons of water per acre is recommended against rhizome johnsongrass, quackgrass and Canada thistle; 5 quarts (5 lbs. A.I.) in 20–60 gallons of water per acre against bermudagrass; and 3–4 quarts (3–4 lbs. A.I.) in 20–30 gallons of water per acre against common milkweed and hemp dogbane.

According to this invention, the herbicidal activity of the isopropylamine salt of glyphosate is markedly potentiated by the aforementioned thiocyanates. Accordingly, application rates from as little as about 0.01 and up to about 5 lbs/acre of the isopropylamine salt of glyphosate, and, preferably, from about 0.1 to about 2 lbs/acre, and, most preferably, from about 0.1 to about 0.5 lb/acre, can now be utilized in conjunction with an effective herbicidal potentiating amount of said thiocyanates, at least about 1 lb/acre, generally from about 1 to about 8 lbs/acre, and, preferably, from about 2 to about 8 lbs/acre. However, based on economic factors, it is most preferred to use from about 2 to about 4 lbs/acre of said thiocyanates. The recommended application rates of the isopropylamine salt of glyphosate to effectively control weeds may be substantially reduced when used in conjunction with said thiocyanates as herein described.

In the herbicidal compositions of the invention, the thiocyanate: the isopropylamine salt of glyphosate weight ratio at which the herbicidal response is synergistic generally lies within the range of from about 0.2:1 to about 800:1, and, preferably, from about 1:1 to about 80:1, and, most preferably, from about 4:1 to about 40:1. For spraying purposes, both ingredients are generally dispersed or suspended in a sufficient amount of water to give complete and uniform coverage of the target weeds and the spray mix can be advantageously applied by conventional herbicide ground spraying equipment. Although it is convenient to apply both the isopropylamine salt of glyphosate and thiocyanate components simultaneously in one formulation, each can be applied substantially simultaneously in separate formulations with the effect of a combined application.

The compositions according to the invention are obtained in known manner by intimately mixing the two synergistic components with suitable inert solid or liquid carriers, preferably water, which are inert toward the active components. Water-dispersible premix concentrates such as, for example, emulsifiable and suspendible liquid concentrates, wherein the concentration of active components may range from about 10 to about 90 percent by weight are advantageous for storing purposes. When required for use, simple admixture of the pre-mix concentrate with water to the desired application dosage is all that is necessary.

Advantageous compositions for spraying purposes are aqueous mixes containing, per gallon of composition, from about 0.00125 to about 5 pounds, and, preferably, from about 0.0125 to about 4 pounds, and, most preferably, from about 0.025 to about 1 pounds, of the isopropylamine salt of glyphosate in combination with from about 1 to about 4 pounds of thiocyanate compound. In preparing tank mixes, a gallon of such composition may be diluted with from about 20 to about 60 gallons of water for spraying purposes.

Formulations will generally contain one or more surfactants to promote rapid dispersion of the two synergistic components in aqueous medium to form stable, sprayable suspensions. Non-ionic surfactants are preferred and particularly suitable is the nonionic surfactant commercially available under the tradename "Ortho X-77" from the Chevron Chemical Co., the principal functioning agents of which are alkylarylpolyoxyethylene glycols, free fatty acids and isopropanol. However, when using Roundup, the aforementioned commercial formulation of the isopropylamine salt of glyphosate, additional surfactants may not be required since the product is reported to be already formulated with a surfactant.

The subject invention thus provides a herbicidal composition comprising a mixture of an effective herbicidal amount of the isopropylamine salt of glyphosate and an effective herbicidal potentiating amount of the thiocyanate component. It also provides a method of herbicidally controlling weeds by directly contacting said weeds with an effective herbicidal amount of the isopropylamine salt of glyphosate and an effecting potentiating amount of the thiocyanate component.

The following examples provide further illustrations demonstrating the enhanced response in weed control obtained from application of the two synergistic components.

EXAMPLE 1

This example demonstrates the synergistic response of the isopropylamine salt of glyphosate, (A.I.) and ammonium thiocyanate in combined application to field grown weeds.

The A.I. was utilized as the commercial product, Roundup, containing 4 lbs/gal of the A.I., and was diluted using water. Ammonium thiocyanate was utilized as the commercial product, Intensify, containing 4 lbs/gallon of ammonium thiocyanate, and was diluted using water.

Test plots measuring 10×10 feet were established in a mown field. Several weed species were present including the following grassy weeds, broadleaf weeds, and yellow nutsedge:
  Ryegrass: (*Secale cereale*)
  Mixed Crabgrass: (*Digitaria spp.*)
  Mixed Foxtails: (*Setaria spp.*)
  Mixed Bluegrass: (*Poa spp.*)
  Mixed Fescues: (*Festuca spp.*)
  Canada Thistle: (*Cirsium arvense*)
  Chickweed: (*Stellaria media*)
  Common Dandelion: (*Taraxacum efficinale*)
  Yellow Nutsedge: (*Cyperus esculentus*)

Mowing was discontinued. Approximately one week later, when the weeds were at an average height of 4-5", the plots were sprayed with aqueous formulations of the test compounds. The quantities sprayed were such that the amount of each test compound applied corresponded to the desired application rate in pound(s) per acre. In control plots the test compounds were applied alone at various application rates, whereas in test plots, solutions containing both compounds were applied.

Thirty-one days after spraying, the control and test plots were rated visually in terms of percent control ranging from 0% to 100%; with 0% representing no control and 100% representing complete kill. All types of plant injury were taken into consideration. An overall rating was used which included all the species present.

The results of this test are listed in Table I in the column headed by the symbol "O" (indicating the "observed" results). These results are compared with the expected results, shown in the columns headed by the symbol "E", derived from the control data using Limpel's formula (Limpel et al, 1962, "Weed Control by Dimethylchloroterephthalate Alone and in Certain Combinations," Proc. NEWCC., Vol. 16, pp. 48-53):

$$E = X + Y - XY/100$$

where:
  X = observed percent activity when one of the compounds is used alone, and
  Y = observed percent activity when the other compound is used alone.

An asterisk (*) is used to indicate the tests where the results show synergism, i.e., where the observed result exceeds the expected result. It is clear from the table that synergism was observed at several of the rates tested.

TABLE I

| HERBICIDE SYNERGISM TEST RESULTS | | | |
|---|---|---|---|
| Test Compounds: | | | |
| A: The isopropylamine salt of glyphosate | | | |
| B: NH₄SCN | | | |
| Applied to Field Grown Weeds | | | |
| Percent Control - O: Observed; E: Expected | | | |
| Application Rates (lb/acre) | | | |
| A | B | O | E |
| Control Data: | | | |
| 1.0 | — | 89 | |
| 0.5 | — | 33 | |
| 0.25 | — | 11 | |
| 0.125 | — | 0 | |
| 0.0625 | — | 17 | |
| — | 2 | 6 | |
| Test Data: | | | |
| 1.0 | 2 | 89 | 90 |
| 0.5 | 2 | 44* | 37 |
| 0.25 | 2 | 22* | 16 |
| 0.125 | 2 | 28* | 6 |
| 0.0625 | 2 | 11 | 22 |

EXAMPLE 2

This example demonstrates the synergistic response of the isopropylamine salt of glyphosate and ammonium thiocyanate in combined application to the weed, lambsquarters. The glyphosate and ammonium thiocyanate were utilized as the commercial products stated in Example 1.

Plastic pots measuring 15×15 cm were filled to a depth of 12 cm with growing medium containing sphagnum peat moss, horticultural vermiculite, processed bark, composted pine bark and washed granite sand. Each pot was seeded with common lambsquarters (*Chenopodium album*) seeds. The pots were placed in a greenhouse and watered regularly.

Six weeks after seeding, the plants were sprayed with aqueous formulations of the test compounds. The quantities sprayed were such that the amount of each test compound applied per pot corresponded to the desired application rate in pounds per acre. In control pots the test compounds were applied alone at various application rates, whereas in the test pots, solutions containing both compounds were applied. Additional pots not treated at all were used as standards for measuring the extent of weed control occurring in the treated pots. All pots were returned to the greenhouse bench and watered regularly.

Two weeks after spraying, the control and test pots were compared to the standards and the weed plants in each pot were rated visually in terms of percent control ranging from 0% to 100%, with 0% representing the same degree of growth as the standard and 100% representing complete kill of all the plants in the pot. All types of plant injury were taken into consideration.

The results of this test are listed in Table II using the same format as Example 1. It is clear from the table that synergism was observed at most of the rates tested.

TABLE II

HERBICIDE SYNERGISM TEST RESULTS

Test Compounds:
A. The isoproplyamine salt of glyphosate
B. NH4SCN
Applied to Lambsquaters (*Chenopodium album*)
Percent Damage - O: Observed; E: Expected

| Application Rates lb/acre | | | |
|---|---|---|---|
| A | B | O | E |
| Control Data: | | | |
| .0625 | — | 0 | |
| .125 | — | 0 | |
| .25 | — | 2 | |
| .5 | — | 10 | |
| — | 2 | 0 | |
| — | 4 | 4 | |
| — | 8 | 10 | |
| Test Data: | | | |
| .0625 | 2 | 6* | 0 |
| .0625 | 4 | 10* | 4 |
| .0625 | 8 | 27* | 10 |
| .125 | 2 | 8* | 0 |
| .125 | 4 | 14* | 4 |
| .125 | 8 | 49* | 10 |
| .25 | 2 | 8* | 2 |
| .25 | 4 | 29* | 6 |
| .25 | 8 | 45* | 12 |
| .5 | 2 | 4 | 10 |
| .5 | 4 | 25* | 14 |
| .5 | 8 | 53* | 19 |

We claim:

1. A method of herbicidally controlling weeds selected from the groups consisting of annual grasses, annual broadleaves, perennial grasses and perennial broadleaves by contacting said weeds with a herbicidally effective amount of a composition sufficient to provide from about 0.1 to about 0.5 pound per acre of the isopropylamine salt of glyphosate and an effective potentiating amount of from about 2 to about 4 pounds per acre of ammonium thiocyanate, wherein the weight ratio of ammonium thiocyanate to the isopropylamine salt of glyphosate in the composition is within the range of from about 4:1 to about 40:1, sufficient to enhance the herbicidal activity of the glyphosate.

2. A method according to claim 1 wherein the weeds are selected from the group consisting of ryegrass, mixed crabgrass, mixed foxtails, mixed bluegrass, mixed fescues, Canada thistle, chickweed, common dandelion, yellow nutsedge, common lambsquarter and johnsongrass.

* * * * *